(12) United States Patent
Nakamura et al.

(10) Patent No.: US 6,384,231 B1
(45) Date of Patent: May 7, 2002

(54) METHOD OF PRODUCING 2,4-OXAZOLIDINEDIONES AND METAL SALTS THEREOF

(75) Inventors: Keiko Nakamura, Ibaraki; Takashi Kamikawa, Nara, both of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/955,052

(22) Filed: Sep. 19, 2001

(30) Foreign Application Priority Data

Sep. 21, 2000 (JP) .................... 2000-286893
Sep. 21, 2000 (JP) .................... 2000-286894
Sep. 21, 2000 (JP) .................... 2000-286900

(51) Int. Cl.[7] ......................................... C07D 263/44
(52) U.S. Cl. ..................................................... 548/226
(58) Field of Search ......................................... 548/226

(56) References Cited

U.S. PATENT DOCUMENTS

| | | | | |
|---|---|---|---|---|
| 2,338,064 A | * | 12/1943 | Stoughton | 548/226 |
| 2,338,220 A | * | 1/1944 | Wallingford | 548/226 |
| 2,349,313 A | * | 5/1944 | Stoughton | 548/226 |
| 2,349,795 A | * | 5/1944 | Stoughton | 548/226 |

FOREIGN PATENT DOCUMENTS

| | | |
|---|---|---|
| EP | 0 889 040 A1 | 1/1999 |
| JP | 9-48769 | 2/1997 |
| JP | 11-21281 | 1/1999 |

OTHER PUBLICATIONS

R.W. Stoughton, "5–5–Dialkyl-2-4-oxazolidinediones[1,2]", J. Am. Chem. Society, vol. 63, (Sep. 1941), pp. 2376–2379.
V.H. Wallingford et al., "Alkyl Carbonates in Synthetic Chemistry. VI. Condensation with a–Hydroxy Amides. A New Method for Preparing 2,4–Oxazolidinediones[1]", J. Am. Chem. Society, vol. 67, (Apr. 1945), pp. 522–523.

* cited by examiner

Primary Examiner—Fiona T. Powers
(74) Attorney, Agent, or Firm—Sughrue Mion, PLLC

(57) ABSTRACT

A method of producing a metal salt of 2,4-oxazolidinedione of the general formula (III) wherein a 2hydroxycarboxylate fo the general formula (I), urea and a metal alkoxide of the formula (II) are reacted in an aromatic hydrocarbon; or a 2-hydroxycarboxylate of the general formula (I) and a metal alkoxide of the formula (II) are added to urea, and, then, they are reacted is provided:

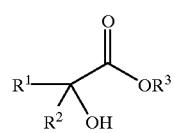

(I)

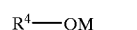

(II)

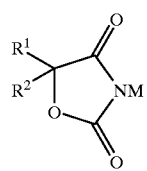

(III)

wherein, $R^1$ and $R^2$ are each independently represent a hydrogen atom or a lower alkyl group, $R^3$ represents a lower alkyl group, $R^4$ represents a lower alkyl group, and M represents an alkali metal atom; and also provided is a method of producing a 2,4-oxazolidinedione of the general formula (IV)

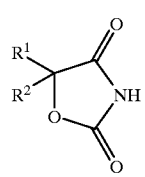

(IV)

wherein a metal salt of 2,4-oxazolidinedione of the general formula (III) is added to an aqueous solution of an acid.

16 Claims, No Drawings

METHOD OF PRODUCING 2,4-OXAZOLIDINEDIONES AND METAL SALTS THEREOF

BACKGROUND OF THE INVENTION

The present invention relates to a method of producing 2,4-oxazolidinediones and metal salts thereof.

2,4-oxazolidinediones and metal salts thereof are compounds useful as an intermediate of a medicine.

As a method of producing metal salts of 2,4-oxazolidinediones, known are a method in which alcohol is used singly as a solvent, and a 2-hydroxycarboxylate, urea and a metal alkoxide are reacted in this solvent, a method in which a 2-hydroxycarboxylate and urea are added to a mixture of a metal alkoxide and a solvent and, then, they are mixed and reacted, and the like [J. Am. Chem. Soc., 63, 2376 (1941)]. However, the former method has a problem that the yield of the resulting metal salt of a 2,4-oxazolidinedione is low, and the latter method has a problem that relatively large amount of by-products are produced simultaneously.

Further, as a method of producing 2,4-oxazolidinediones, there is known a method in which a 2-hydroxycarboxylate, urea and a metal alkoxide are reacted in a solvent to obtain a reaction mixture containing a metal salt of a 2,4-oxazolidinedione, and an aqueous solution of an acid is added, to the resulted reaction mixture [J. Am. Chem. Soc., 63, 2376 (1941)]. However, also this production method has a problem that the yield of the resulting 2,4-oxazolidinedione is not sufficient.

The present inventors have intensively studied for solving the above-mentioned conventional problems, and resultantly found that a metal salt of 2, 4-oxazolidinedione can be obtained efficiently by reacting a 2-hydroxycaboxylate, urea and a metal alkoxide in an aromatic hydrocarbon.

Also, the present inventors have found that when a 2-hydroxycarboxylate and a metal alkoxide are added to urea, the amount of by-products produced is small.

Further, the present inventors have intensively studied for developing a method which can produce a 2,4-oxazolidinedione from a metal salt of 2,4-oxazolidinedione with high yield, and resultantly found that by adding a metal salt of 2,4-oxazolidinedione to an aqueous solution of an acid, the intended 2,4-oxazolidinedione can be obtained at high yield. Thus, the present invention was completed.

SUMMARY OF THE INVENTION

The present invention provides a method of producing a metal salt of 2,4-oxazolidinedione of the general formula (III) wherein a 2-hydroxycarboxylate of the general formula (I), urea and a metal alkoxide of the formula (II) are reacted in an aromatic hydrocarbon:

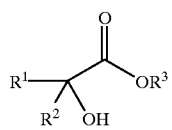

(I)

wherein, $R^1$ and $R^2$ each independently represent a hydrogen atom or a lower alkyl group, and $R^3$ represents a lower alkyl group;

$R^4$—OM (II)

wherein, $R^4$ represents a lower alkyl group, and M represents an alkali metal atom;

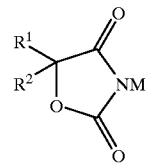

(III)

wherein, $R^1$, $R^2$ and M have the same meanings as described above. (hereinafter, this method is referred to as Metal salt production method 1).

The present invention also provides a method of producing a metal salt of 2, 4-oxazolidinedione of the general formula (III) wherein a 2-hydroxycarboxylate of the general formula (I) and a metal alkoxide of the formula (II) are added to urea, and, then, they are reacted. (hereinafter, this method is referred to as Metal salt production method 2).

Further, the present Invention provides a method of producing a 2,4-oxazolidinedione of the general formula (IV):

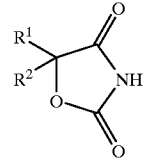

(IV)

wherein, $R^1$ and $R^2$ have the same meanings as described above, wherein a metal salt of 2,4-oxazolidinedione of the general formula (III) is added to an aqueous solution of an acid. (hereinafter, this method is referred to as Production method 3).

DETAILED DESCRIPTION OF THE PREFERRED EMBODIMENTS

As the lower alkyl group represented by $R^1$, $R^2$ and $R^3$ in the general formula (I) and as the lower alkyl group represented by $R^1$ and $R^2$ in the general formulae (III) and (IV) for example, a methyl group, ethyl group, propyl group, butyl group and the like are listed.

Examples of such 2-hydroxycarboxylates include methyl glycolate, ethyl glycolate, propyl glycolate, butyl glycolate, methyl 2-hydroxypropionate, ethyl 2-hydroxypropionate, propyl 2-hydroxypropionate, butyl 2-hydroxypropionate, methyl 2-hydroxyisobutyrate, ethyl 2-hydroxyisobutyrate, propyl 2-hydroxyisobutyrate, butyl 2-hydroxyisobutyrate, methyl 2-hydroxyvalerate, ethyl 2-hydroxyvalerate, propyl 2-hydroxyvalerate, butyl 2-hydroxyvalerate, methyl 2-hydroxyhexanoate, ethyl 2-hydroxyhexanoate, propyl 2-hydroxyhexanoate, butyl 2-hydroxyhexanoate, methyl 2-hydroxy-2-methylbutyrate, ethyl 2-hydroxy-2-methylbutyrate, propyl 2-hydroxy-2-methylbutyrate, butyl 2-hydroxy-2-methylbutyrate and the like.

In any of Metal salt production method 1 and Metal Salt production method 2, the use amount of urea is usually from about 1 to 5-fold mol, preferably from about 1 to 3-fold mol based on the 2-hydroxycarboxylate.

As the lower alkyl group represented by $R^4$ in the general formula (II), for example, a methyl group, ethyl group, propyl group, butyl group and the like are listed. In the general formula (II), or in the general formula (III), examples of M include alkali metal atoms such as a lithium atom, sodium atom, potassium atom, and the like. Examples of such metal alkoxides include lithium methoxide, lithium ethoxide, sodium methoxide, sodium ethoxide, potassium methoxide, potassium ethoxide and the like.

In any of Metal salt production method 1 and Metal salt production method 2, the use amount the metal alkoxide is usually from about 1 to 3-fold mol, preferably from about 1 to 2-fold mol, further preferably from about 1 to 1.5-fold mol, based on the 2-hydroxycarboxylate.

In Metal salt production method 1, such a 2-hydroxycarboxylate, urea and a metal alkoxide are reacted in an aromatic hydrocarbon. As the aromatic hydrocarbon, for example, benzene, toluene, xylene, ethylbenzene and the like are listed. These may be used alone or in admixture of two or more. The use amount of the aromatic hydrocarbon is usually from about 0.5 to 10-fold by weight, preferably from about 1 to 5-fold by weight, further preferably from about 2 to 3-fold by weight, based on the 2-hydroxycarboxylate.

The reaction in Metal salt production method 1 of the present invention is conducted in an aromatic hydrocarbon, and alcohol may be allowed to be further present in this reaction. As the alcohol, for example, methanol, ethanol and the like are listed. When reacted in the presence of alcohol, the use amount thereof is usually 10-fold by weight or less, preferably 3-fold by weight or less, more preferably 0.7-fold by weight or less, based on the aromatic hydrocarbon.

For carrying out the reaction in Metal salt production method 1, for example, an aromatic hydrocarbon, urea, a 2-hydroxycarboxylate and a metal alkoxide are mixed. The reaction temperature is usually 50° C. or more and 80° C. or less, preferably 60° C. or more and 70° C. or less. When reacted in the presence of alcohol, this alcohol may also be supplied, together with a metal alkoxide, as a metal alkoxide alcohol solution in which the metal alkoxide is dissolved.

The reaction may also be conducted under reduced pressure, for example, under a pressure of from about 0.080 to 0.093 MPa. The reaction time is preferably from about 2 to 5 hours, usually.

In Metal salt production method 2, a 2-hydroxycarboxylate and a metal alkoxide are added to urea and, then, they are reacted. Usually, a 2-hydroxycarboxylate and a metal alkoxide are added to a mixture o urea and a solvent.

As the solvent, aromatic hydrocarbons, alcohols and the like are listed, and preferable are aromatic hydrocarbons. As the aromatic hydrocarbon, for example, benzene, toluene, xylene, ethylbenzene and the like are listed. As the alcohol, for example, methanol, ethanol and the like are listed. These may be used alone or in combination of two or more. The use amount of a solvent in Metal salt production method 2 is usually from about 0.5 to 10-fold by weight, preferably from about 1 to 5-fold by weight, more preferably from about 2 to 3-fold by weight based on the used 2-hydroxyoarboxylate.

The reaction of Metal salt production method 2 is usually conducted by adding a 2 -hydroxycarboxylate and a metal alkoxide to a mixture of urea and a solvent. The reaction time is usually 50° C. or more and 80° C. or less, preferably 60° C. or more and 70° C. or less. When alcohol is used as a solvent, this alcohol may also be supplied, together with the metal alkoxide, as a metal alkoxide alcohol solution in which the metal alkoxide is dissolved.

The reaction of Metal salt production method 2 may also be conducted under reduced pressure, for example, under reduced pressure of from about 0.080 to 0.093 MPa. The reaction time is preferably from about 2 to 5 hours, usually.

Thus, metal salts of 2,4-oxazolidinediones of the general formula (III) are produced by Metal salt production method 1 or Metal salt production method 2. When alcohol is used, a reaction mixture after the reaction may be separated in some cases into two layers, an aromatic hydrocarbon layer and an alcohol layer. Since the intended metal salt of 2,4-oxazolidinedione Is dissolved in the alcohol layer, if the alcohol layer is separated, the intended metal salt of 2,4-oxazolidinedione can be obtained as an alcohol solution.

As thus obtained metal salts of 2,4-oxazolidinediones, for example, lithium salts, sodium salts, potassium salts and the like of 2,4-oxazolidinedione, 5-methyl-5-ethyl-2,4-oxazolidinedione, 5,5-dimethyl-2,4-oxazolidinedione, 5-propyl-2,4-oxazolidinedione, 5-butyl-2,4-oxazolidinedione, 5-ethyl-2,4-oxazolidlinedione and the like, are listed.

Thus obtained metal salt of 2,4-oxazolidinedione can be reacted, for example, with an acid to obtain a 2,4-oxazolidinedione of the general formula (IV).

As the acid, for example, hydrochloric acid, sulfuric acid and the like are listed, and the use amount thereof is usually 0.9-fold equivalent or more based on the 2,4-oxazolidinedione.

For reacting with an acid, for example, an acid may be added to the metal salt of 2,4-oxazolidinedione. When alcohol is used and the metal salt of 2,4-oxazolidinedione are obtained as an alcohol solution, an acid may be added to this alcohol solution. An acid may also be added, for example, as a solution dissolved in water or alcohol such as methanol, ethanol or the likes.

Particularly preferable is a method in which a metal salt of 2,4-oxazolidinedione of the general formula (III) is added to an aqueous solution of an acid, which is Production method 3 of the present invention. Production method 3 is effective also for metal salts of 2,4-oxazolidinediones of the general formula (III) produced by methods effected under other conditions than in Metal salt production method 1 and Metal salt production method 2. For example, production method 3 is a preferable method also when 2,4-oxazolidinediones of the general formula (IV) are obtained from those produced without using an aromatic hydrocarbon as a solvent, or from those produced by a method in which a 2-hydroxycarboxylate and urea are added to a mixture of a metal alkoxide and a solvent and they are reacted.

Also in Production method 3, a metal salt of 2,4-oxazolidinedione may be added singly to an aqueous solution of an acid. Alternatively, it may also be added as a solution of a metal salt of 2,4-oxazolidinedione dissolved in a solvent. As the solvent used in the solution of a metal salt of 2,4-oxazolidinedione, for example, the same alcohols, aromatic hydrocarbons and the like as described above are listed.

The solution of metal salt of 2,4-oxazolidinedione may be obtained by a method in which a metal salt of 2,4-oxazolidinedione is dissolved in a solvent. It may also be a reaction mixture obtained by the above-mentioned method, for example, a method when an aromatic hydrocarbon and alcohol are used in the above-mentioned reaction. Further, it may also be an alcohol layer obtained by liquid separation.

In Production method 3, hydrochloric acid, sulfuric acid and the like are listed, for example, as the acid. The use amount thereof is usually 0.9-fold equivalent or more, preferably 1-fold equivalent or more and 4-fold equivalent or less, more preferably 1-fold equivalent or more and 2-fold equivalent or less, based on the 2,4-oxazolidinedione.

The use amount of water in an aqueous solution of an acid is usually from 0.5 to 10-fold by weight, preferably from 0.8 to 3-fold by weight, based on the 2,4-oxazolidinedione.

The aqueous solution of an acid may contain a neutral salt. As the neutral salt, for example, lithium chloride, sodium chloride, potassium chloride, lithium sulfate, sodium sulfate, potassium sulfate and the like are listed. When a neutral salt is used, its content in an aqueous solution is not particularly restricted, and for example, it may also be saturated in an aqueous solution of an acid. Further, it may be used excessively, or may be precipitated, providing the operation is not disturbed.

The temperature in adding a metal salt of 2,4-oxazolidinedione to an aqueous solution of an acid is usually from 0° C. to 10° C.

In adding a metal salt of 2,4 -oxazolidinedione to an aqueous solution of an acid, if a hydrophobic solvent is previously added to the aqueous solution of an acid, and the metal salt of 2,4-oxazolidinedione is added to this mixture of the aqueous solution of an acid and the hydrophobic solvent, then, the resulting 2,4-oxazolidinedione is extracted from the aqueous solution of an acid into the hydrophobic solvent, and the intended 2,4-oxazolidinedione can be easily obtained as a hydrophobic solvent solution, by effecting liquid separation to give a hydrophobic solvent layer.

The hydrophobic solvent may be a solvent that is not compatible with water and can dissolve 2,4-oxazolidinediones, and for example, ketones such as methyl isobutyl ketone, methyl ethyl ketone and the like are listed. Such hydrophobic solvents may be used alone or in combination of two or more. The use amount of the hydrophobic solvent is usually from about 2 to 10-fold by weight based on the metal salt of 2,4-oxazolidinedione.

Thus, 2,4-oxazolidinediones of the general formula (IV) are obtained by Production method 3 and other methods. Examples of such 2,4-oxazolidinediones include 2,4-oxazolidinedione, 5-methyl-5-ethyl-2,4-oxazolidinedione, 5,5-dimethyl-2,4-oxazolidinedione, 5-propyl-2,4-oxazolidinedione, 5-butyl-2,4-ozazolidinedione, 5-ethyl-2,4-oxazolidinedione and the like.

According to Metal salt production method 1 of the present invention, a metal salt of 2,4-oxazolidinedione can be produced with high yield from a 2-hydroxycarboxylate.

According to Metal salt production method 2 of the present invention, a metal salt of 2,4-oxazolidinedione can be produced from a 2-hydroxycarboxylate, urea and a metal alkoxide, while suppressing production of by-products.

Further, according to Production method 3, a 2,4-oxazolidinedione can be produced with high yield from a metal salt of 2,4-oxazolidinedione.

EXAMPLES

The following examples illustrate the present invention further in detail below, but do not limit the scope of the invention.

Example 1

Toluene (150 g), urea (30 g, 0.5 mol), methyl 2-hydroxyisobutyrate (59.1 g, 0.5 mol) and a metal alkoxides alcohol solution (96.5 g), which was prepared by dissolving 27 g (0.5 mol) of sodium methoxide into methanol (69.5 g), were mixed under reduced pressure (0.086 MPa) at room temperature Then, the mixture was heated up to 70° C. and stirred for 6 hours under the same pressure and the same temperature to obtain a reaction product, separated into two layers, a toluene layer and a methanol layer containing a sodium salt of 5,5-dimethyl-2,4-oxazolidinedione.

The methanol layer was separated at room temperature from this reaction mixture, and a portion of 100 mg was collected from the resulted methanol layer. To this was added a mixture of 25.2% hydrochloric acid and methanol (mixed solution of 1 part by weight of hydrochloric acid, 2 parts by weight of water and 1 part by weight of methanol) until pH reached 1 or less. Then, the resulting mixture was introduced into a gas chromatograph, to confirm a peak of 5,5-dimethyl-2,4-oxazolidinedione and peaks of by-products. The content of a sodium salt of 5,5-dimethyl-2,4-oxazolidinedione in the methanol layer, calculated from the peak area, was 56.3 g (yield: 87.2%). Also, the existing ratio of a sodium salt of 5.5-dimethyl-2,4-oxazolidinedione against the total amount of by-products and a sodium salt of 5,5-dimethyl-2,4-oxazolidinedione, in the methanol layer, was calculated from the peak areas. The results are shown in Table 1.

Comparative Example 1

The same operation was conducted as in Example 1 except that ethanol (150 g) was used instead of toluene, to obtain an ethanol solution containing a sodium salt of 5,5-dimethyl-2,4-oxazolidinedione.

A portion of 100 mg was collected from this ethanol solution. To this was added a mixture of 25.2% hydrochloric acid and methanol (mixed solution of 1 part by weight of hydrochloric acid, 2 parts by weight of water and 1 part by weight of methanol) until pH reached 1 or less. Then, the mixture was introduced into a gas chromatograph, to confirm a peak of 5,5-dimethyl-2,4-oxazolidinedione. The content of a sodium salt of 5,5-dimethyl-2,4-oxazolidinedione in the ethanol layer, calculated from the peak area, was 53 g (yield: 82.2%).

Example 2

(In the Case of Use of Toluene as Solvent)

A mixture of 30 g (0.5 mol) of urea and toluene (150 g) was heated up to 70° C. under reduced pressure (0.086 MPa). To this was added dropwise 59.1 g (0.5 mol) of methyl 2-hydroxyisobutyrate and a metal alkoxides alcohol solution (96.5 g), which was prepared by dissolving 27 g (0.5 mol) of sodium methoxide into methanol (69.5 g), under the same pressure and the same temperature over 3 hours while stirring. Then, it the mixture was stirred for 3 hours under the same pressure and the same temperature, to obtain a reaction mixture. The resulting reaction mixture had been separated into two layers, a toluene layer and a methanol layer, and the methanol layer contained a sodium salt of 5,5-dimethyl-2,4-oxazolidinedione.

This reaction mixture was separated at room temperature to isolate the methanol layer, and a portion of 100 mg was collected from the methanol layer. To this was added a mixture of 25.2% hydrochloric acid and methanol (mixed solution of 1 part by weight of hydrochloric acid, 2 parts by weight of water and 1 part by weight of methanol) until pH reached 1 or less. Then, the mixture was introduced into a gas chromatograph, to confirm a peak of 5,5-dimethyl-2,4-oxazolidinedione and peaks of by-products. The existing ratio of a sodium salt of 5,5-dimethyl-2,4-oxazolidinedione against the total amount of by-products and a sodium salt of 5.5-dimethyl-2,4-oxazolidinedione, in the methanol layer, was calculated from the peak areas. The results are shown in Table 1.

TABLE 1

| | Existing ratio of sodium salt of 5,5-dimethyl-2,4-oxazolidinedione | Existing ratio of by-product |
|---|---|---|
| Example 2 | 95.7% | 4.3% |
| Example 1 | 88.7% | 11.3% |

Unit is area percentage

Example 3
(In the Case of Use of Ethanol as Solvent)

The same operation was conducted as in Example 2 except that ethanol (150 g) was used instead of toluene, to obtain an ethanol-methanol solution containing a sodium salt of 5, 5-dimethyl-2,4-oxazolidinedione.

A portion of 100 mg was collected from this ethanol solution. To this was added a mixture of 25.2% hydrochloric acid and methanol (mixed solution of 1 part by weight of hydrochloric acid, 2 parts by weight of water and 1 part by weight of methanol) until pH reached 1 or less. Then, the mixture was introduced into a gas chromatograph, to confirm a peak of 5,5-dimethyl-2,4-oxazolidinedione and peaks of by-products. The existing ratio of a sodium salt of 5,5-dimethyl-2,4-oxazolidinedione against the total amount of by-products and a sodium salt of 5,5-dimethyl-2,4-oxazolidinedione, in the ethanol layer, was calculated from the peak areas. The results are shown in Table 2.

Comparative Example 2

The same operation was conducted as in Example 1 except that ethanol (150 g) was used instead of toluene, to obtain an ethanol solution containing a sodium salt of 5,5-dimethyl-2,4-oxazolidinedione.

A portion of 100 mg was collected from this ethanol solution. To this was added a mixture of 25.2% hydrochloric acid and methanol (mixed solution of 1 part by weight of hydrochloric acid, 2 parts by weight of water and 1 part by weight of methanol) until pH reached 1 or less. Then, the mixture was introduced into a gas chromatograph, to confirm a peak of 5,5-dimethyl-2,4-oxazolidinedione and peaks of by-products. The existing ratio of a sodium salt of 5,5-dimethyl-2,4-oxazolidinedione against the total amount of by-products and a sodium salt of 5,5-dimethyl-2,4-oxazolidinedione, in the ethanol layer, was calculated from the peak areas. The results are shown in Table 2.

TABLE 2

| | Existing ratio of sodium salt of 5,5-dimethyl-2,4-oxazolidinedione | Existing ratio of by-product |
|---|---|---|
| Example 3 | 87.4% | 12.6% |
| Comparative example 2 | 83.2% | 16.8% |

Unit is area percentage

Example 4

A mixture of 30 g (0.5 mol) of urea and toluene (150 g) was heated up to 70° C. under reduced pressure (0.086 MPa). To this was added dropwise 59.1 g (0.5 mol) of methyl 2-hydroxyisobutyrate and a metal alkoxides alcohol solution (96.5 g), which was prepared by dissolving 27 g (0.5 mol) of sodium methoxide into methanol (69.5 g), under the same temperature over 3 hours while stirring. Then, the mixture was stirred for 3 hours at the same temperature, to obtain a reaction mixture separated into two layers, a toluene layer and a methanol layer containing a sodium salt of 5,5-dimethyl-2,4-oxazolidinedione. Then, the mixture was subjected to liquid-separation to isolate the methanol layer. This methanol layer was a methanol solution of a sodium salt of 5,5-dimethyl-2. 4-oxazolidinedione. Then, this methanol solution was divided into five portions uniformly.

One of the five-divided solutions was added, at a temperature from 0 to 10° C., to a mixture of 27.7 g of an aqueous hydrochloric acid solution (containing 3.75 g (0.1 mol) of hydrochloric acid and 23.95 g of water) and 60 g of methyl isobutyl ketone. Then, the mixture was subjected to liquid-separation to isolate the methyl isobutyl ketone layer, and the resulted methyl isobutyl ketone layer was analyzed by gas chromatography, to find a yield of 5,5-dimethyl-2,4-oxazolidinedione of 10.6 g (0.082 mol).

Comparative Example 3

To one of the five-divided solutions in Example 4 was added a mixture of 60 g of methyl isobutyl ketone and 17 g of water. To this was added, at a temperature from 0 to 10° C., 10.7 g of 35% hydrochloric acid (containing 3.75 g (0.1 mol) of hydrochloric acid, and 6.95 g of water). Then, the mixture was subjected to liquid-separation to isolate the methyl isobutyl ketone layer, and the resulted methyl isobutyl ketone layer was analyzed by gas chromatography to find a yield of 5,5-dimethyl-2,4-oxazolidinedione of 9.8 g (0.076 mol).

What is claimed is:

1. A method of producing a metal salt of 2,4-oxazolidinedione of the general formula (III) wherein a 2-hydroxycarboxylate of the general formula (I), urea and a metal alkoxide of the formula (II) are reacted in an aromatic hydrocarbon:

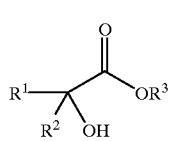
(I)

wherein, $R^1$ and $R^2$ each independently represent a hydrogen atom or a lower alkyl group, and $R^3$ represents a lower alkyl group;

(II)

$$R^4\text{—OM}$$

wherein, $R^4$ represents a lower alkyl group, and M represents go an alkali metal atom; and

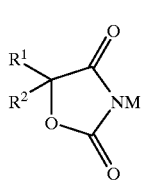
(III)

wherein, $R^1$, $R^2$ and M have the same meanings as described above.

2. The method according to claim 1, wherein the use amount of the aromatic hydrocarbon is from about 0.5 to 10-fold by weight, the use amount of urea is from about 1 to 5-fold mol, and the use amount the metal alkoxide is from about 1 to 3-fold mol, based on the 2-hydroxycarboxylate.

3. The method according to claim 1, wherein the reaction is conducted in the presence of alcohol.

4. The method according to claim 3, wherein the use amount alcohol is 10-fold by weight or less, based on the aromatic hydrocarbon.

5. A method of producing a metal salt of 2,4-oxazolidinedione of the general formula (III) wherein a 2-hydroxycarboxylate of the general formula (I) and a metal alkoxide of the formula (II) are added to urea, and, then, they are reacted:

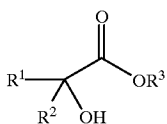
(I)

wherein, $R^1$ and $R^2$ each independently represent a hydrogen atom or a lower alkyl group, and $R^3$ represents a lower alkyl group;

(II)

wherein, $R^4$ represents a lower alkyl group, and M represents an alkali metal atom; and

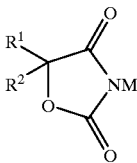
(III)

wherein, $R^1$, $R^2$ and M have the same meanings as described above.

6. The method according to claim 5, wherein a 2-hydroxycarboxylate and a metal alkoxide are added to a mixture of urea and a solvent.

7. The method according to claim 5, wherein the solvent is selected from aromatic hydrocarbons and mixtures comprising an aromatic hydrocarbon and an alcohol.

8. The method according to claim 5, wherein the use amount of urea is from about 1 to 5-fold mol, and the use amount the metal alkoxide Is from about 1 to 3-fold mol, based on the 2-hydroxycarboxylate.

9. A method of producing a 2,4-oxazolidinedione of the general formula (IV):

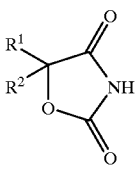
(IV)

wherein, $R^1$ and $R^2$ each independently represent a hydrogen atom or a lower alkyl group, wherein a metal salt of 2,4-oxazolidinedione of the general formula (III) is added to an aqueous solution of an acid:

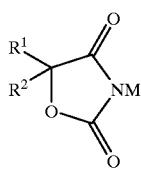
(III)

wherein, $R^1$ and $R^2$ have the same meanings as described above, and M represents an alkali metal atom.

10. The method according to claim 9, wherein a solution of metal salt of 2,4-oxazolidinedione dissolved in a solvent is added to an aqueous solution of an acid.

11. The method according to claim 9, wherein the use amount the acid is 0.9-fold equivalent or more based on the 2,4-oxazolidinedione.

12. The method according to claim 11, wherein the use amount of water in an aqueous solution of an acid is from 0.5 to 10-fold by weight based on the 2,4-oxazolidinedione.

13. The method according to claim 9, wherein the metal salt of 2,4-oxazolidinedione is added to a mixture of the aqueous solution of an acid and the hydrophobic solvent.

14. The method according to claim 13, wherein the use amount of the hydrophobic solvent is from about 2 to 10-fold by weight based on the metal salt of 2,4-oxazolidinedione.

15. The method according to claim 10, wherein the solution of metal salt of 2,4-oxazolidinedione dissolved is a reaction mixture obtained by reacting a 2-hydroxycarboxylate of the general formula (I), urea and a metal alkoxide of the formula (II) in a solvent:

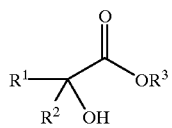
(I)

wherein, $R^1$ and $R^2$ each independently represent a hydrogen atom or a lower alkyl group, and $R^3$ represents a lower alkyl group;

(II)

wherein, $R^4$ represents a lower alkyl group, and M represents an alkali metal atom.

16. The method according to claim 15, wherein the use amount of the solvent is from about 0.5 to 10-fold by weight, tho use amount of urea is from about 1 to 5-fold mol, and the use amount the metal alkoxside is from about 1 to 3-fold mol, based on the 2-hydroxycarboxylate.

* * * * *